United States Patent
Gao et al.

(10) Patent No.: US 6,953,690 B1
(45) Date of Patent: Oct. 11, 2005

(54) COMPOSITIONS AND METHODS FOR HELPER-FREE PRODUCTION OF RECOMBINANT ADENO-ASSOCIATED VIRUSES

(75) Inventors: Guangping Gao, Rosemont, PA (US); James M. Wilson, Gladwyne, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 98 days.

(21) Appl. No.: 09/665,852

(22) Filed: Sep. 20, 2000

Related U.S. Application Data

(63) Continuation of application No. PCT/US99/05870, filed on Mar. 18, 1999.

(60) Provisional application No. 60/078,908, filed on Mar. 20, 1998.

(51) Int. Cl.$^7$ .......................... C12N 5/00; C12N 15/86; C12N 15/00; A01N 63/00; C07H 21/04
(52) U.S. Cl. ...................... 435/325; 435/455; 435/456; 435/320.1; 424/93.2; 424/93.21; 536/23.1; 536/24.1
(58) Field of Search .......................... 435/172.3, 320.1, 435/369, 69.1, 240.2, 325, 239, 455, 466, 435/456; 424/93.2, 93.21; 536/23.1, 24.1

(56) References Cited

U.S. PATENT DOCUMENTS

| | | | |
|---|---|---|---|
| 5,436,146 A | 7/1995 | Shenk | |
| 5,622,856 A | 4/1997 | Natsoulis | |
| 5,658,776 A | 8/1997 | Flotte et al. | |
| 5,658,785 A | 8/1997 | Johnson | |
| 5,681,731 A | 10/1997 | Lebkowski et al. | |
| 5,756,283 A | 5/1998 | Wilson et al. | |
| 5,837,484 A | 11/1998 | Trempe et al. | |
| 5,856,152 A * | 1/1999 | Wilson et al. | ........... 435/172.3 |
| 5,871,982 A | 2/1999 | Wilson et al. | |
| 6,251,677 B1 | 6/2001 | Wilson et al. | |
| 6,258,595 B1 * | 7/2001 | Gao et al. | ................ 435/320.1 |
| 6,475,769 B1 | 11/2002 | Wilson et al. | |
| 6,485,966 B2 | 11/2002 | Gao et al. | |
| 6,541,258 B2 | 4/2003 | Allen et al. | |
| 2003/0040101 A1 | 2/2003 | Wilson et al. | |
| 2003/0119191 A1 | 6/2003 | Gao et al. | |
| 2004/0018627 A1 * | 1/2004 | Natsoulis et al. | ........... 435/456 |

FOREIGN PATENT DOCUMENTS

| | | |
|---|---|---|
| WO | WO 95/06743 A | 3/1995 |
| WO | WO 95/34670 A | 12/1995 |
| WO | WO 96/13598 A | 5/1996 |
| WO | WO 96/14061 A | 5/1996 |
| WO | WO 96/39530 A | 12/1996 |
| WO | WO 96/40240 A | 12/1996 |
| WO | WO 97/12050 A | 4/1997 |
| WO | WO 97/17458 A | 5/1997 |
| WO | WO 97/26337 A | 7/1997 |
| WO | WO 98/10086 A | 2/1998 |
| WO | WO 98/09657 A | 3/1998 |
| WO | WO 98/10088 A | 3/1998 |
| WO | WO 99/14354 A | 3/1999 |
| WO | WO 99/15685 A | 4/1999 |
| WO | WO00/55342 A1 | 9/2000 |

OTHER PUBLICATIONS

Fields et al. Virology. vol. 2., 3rd edition. 1995. Philadelphia: Lippencott Willims and Wilkins; p. 2183.*
Alkhatib et al. Journal of Virology. 1988; 62 (8): 2718-27, abstract only.*
B. J. Carter, "The Growth Cycle of Adeno-Associated Virus", in *Handbook of Parvoviruses*, ed. Tijsser, CRC Press, Quebec, Canada, pp. 155-168 (1990).
G-P. Gao, "High Titer Adeno-Associated Viral Vectors from a Rep/Cap Cell Line and Hybrid Shuttle Virus", *Human Gene Therapy*, 9:2353-2362 (Nov. 1, 1998).
R. B. Kotin, "Prospects for the Use of Adeno-Associated Virus as a Vector for Human Gene Therapy", *Human Gene Therapy*, 5:793-801 (Jul. 1994).
D. D. Coovert, "Gene Therapy for Muscle Diseases", *Current Opinion in Neurology*, 7(5):463-470 (Oct. 1, 1994).
G-P. Gao et al., "Compositions and Methods for Helper-Free Production of Recombinant Adeno-Associated Viruses", U. S. Appl. No. 09/404,555, filed Sep. 23, 1999.
Berendsen et al, "A Glimpse of the Holy Grail?", Science, 282, pp. 543-642 (Oct. 1998).
Fisher et al, "Recombinant adeno-associated virus for muscle directed gene therapy", Nature Medicine, 3(3): 306-312 (Mar. 1997).
Herzog et al, "Stable gene transfer and expression of human blood coagulation factor IX after intramuscular injection of recombinant adeno-associated virus", Proc. Natl. Acad. Sci. USA, 94:5804-5809 (May 1997).

(Continued)

*Primary Examiner*—Gerry Leffers
*Assistant Examiner*—Maria Marvich
(74) *Attorney, Agent, or Firm*—Howson and Howson

(57) ABSTRACT

A method for producing recombinant adeno-associated virus in the absence of contaminating helper virus or wild-type virus involves culturing a mammalian host cell containing a transgene flanked by adeno-associated virus (AAV) inverse terminal repeats and under the control of regulatory sequences directing expression thereof, an AAV rep sequence and an AAV cap sequence under the control of regulatory sequences directing expression thereof, and the minimum adenovirus DNA required to express an E1a gene product, an E1b gene product and an E2a gene product, and isolating therefrom a recombinant AAV which expresses the transgene in the absence of contaminating helper virus or wildtype AAV. This method obviates a subsequent purification step to purify rAAV from contaminating virus. Also provided are various embodiments of the host cell.

20 Claims, 3 Drawing Sheets

OTHER PUBLICATIONS

Kessler et al, "Gene delivery to skeletal muscle results in sustained expression and systemic delivery of a therapeutic protein", Proc. Natl. Acad. Sci. USA, 93: 14082-14087 (Nov. 1996).

Samulski et al, "Helper-Free Stocks of Recombinant Adeno-associated Viruses: Normal Integration Does Not Require Viral Gene Expression", J. Virol., 63(9): 3822-3828 (Sep. 1989).

* cited by examiner

COMPOSITIONS AND METHODS FOR HELPER-FREE PRODUCTION OF RECOMBINANT ADENO-ASSOCIATED VIRUSES

CROSS-REFERENCE TO RELATED APPLICATIONS

This is a continuation of International Patent Application No. PCT/US99/05870, filed on Mar. 18, 1999, which claims the benefit of the priority of U.S. Patent Application No. 60/078,908, filed on Mar. 20, 1998.

BACKGROUND OF THE INVENTION

Adeno-associated virus (AAV) is a replication-deficient parvovirus, the genome of which is about 4.6 kb in length, including 145 nucleotide inverted terminal repeats (ITRs). Two open reading frames encode a series of rep and cap polypeptides. Rep polypeptides (rep78, rep68, rep62 and rep40) are involved in replication, rescue and integration of the AAV genome. The cap proteins (VP1, VP2 and VP3) form the virion capsid. Flanking the rep and cap open reading frames at the 5' and 3' ends are 145 bp inverted terminal repeats (ITRs), the first 125 bp of which are capable of forming Y- or T-shaped duplex structures. Of importance for the development of AAV vectors, the entire rep and cap domains can be excised and replaced with a therapeutic or reporter transgene [B. J. Carter, in "Handbook of Parvoviruses", ed., P. Tijsser, CRC Press, pp. 155–168 (1990)]. It has been shown that the ITRs represent the minimal sequence required for replication, rescue, packaging, and integration of the AAV genome.

When this nonpathogenic human virus infects a human cell, the viral genome integrates into chromosome 19 resulting in latent infection of the cell. Production of infectious virus and replication of the virus does not occur unless the cell is coinfected with a lytic helper virus, such as adenovirus (Ad) or herpesvirus. Upon infection with a helper virus, the AAV provirus is rescued and amplified, and both AAV and helper virus are produced. The infecting parental ssDNA is expanded to duplex replicating form (RF) DNAs in a rep dependent manner. The rescued AAV genomes are packaged into preformed protein capsids (icosahedral symmetry approximately 20 nm in diameter) and released as infectious virions that have packaged either + or − ss DNA genomes following cell lysis.

AAV possesses unique features that make it attractive as a vector for delivering foreign DNA (i.e., a transgene) to cells, and various groups have studied the potential use of AAV in the treatment of disease states. As used in this application, the term "transgene" means the DNA desired to be delivered to an animal, the DNA being non-AAV DNA. However, progress towards establishing AAV as a transducing vector for the delivery of DNA in the form of a desired transgene has been slow for a variety of reasons.

One obstacle to the use of AAV for delivery of DNA has been lack of highly efficient schemes for encapsidation of recombinant genomes and production of infectious virions. See, R. Kotin, *Hum. Gene Ther.* 5: 793–801 (1994)]. One method which addresses this problem involves transfecting a recombinant AAV (rAAV) (which has the DNA to be delivered, but lacks rep and cap genes) into host cells followed by co-infection with wild-type (wt) AAV (which supplies the rep and cap genes) and adenovirus (which supplies at least the four adenovirus genes: E1, E2, E4 and VAI, which have been stated to be necessary for rAAV production) [see, e.g., Carter, cited above]. However, this method requires mandatory co-infection and leads to unacceptably high levels of wt AAV resulting from non-homologous recombination and contamination of the rAAV produced with wt AAV. The contamination with other viruses or plasmids demands purification of rAAV. Incubation of cells with rAAV in the absence of contaminating wt AAV or helper adenovirus yields little recombinant gene expression.

A widely recognized means for manufacturing transducing AAV virions for gene therapy entails co-transfection with two different, complementing plasmids. One of these plasmids contains a therapeutic or reporter transgene sandwiched between the two cis acting AAV ITRs. The AAV components that are needed for rescue and subsequent packaging of progeny recombinant genome are provided in trans by a second plasmid encoding the viral open reading frames for rep and cap proteins. In this system, the Ad helper functions are provided by a wt adenovirus or by replication-defective adenovirus with the missing E1 gene supplied by HEK 293 cells. Other variants of this method have been described. See, for example, U.S. Pat. No. 5,658,785, which refers to a mammalian host cell stably transfected with a rAAV genome and with AAV rep and cap genes, and a method for producing rAAV by infecting this host cell with a helper virus.

U.S. Pat. No. 5,658,776 refers to packaging systems and processes for packaging AAV vectors in which the AAV p5 promoter is replaced with a heterologous promoter. Alternatively, U.S. Pat. No. 5,622,856 refers to constructs and methods for AAV vector production in which the homologous p5 promoter is moved to a position 3' of the rep genes, optionally flanking the rep/cap genes and repositioned p5 promoter with FRT sequences.

There remains a need in the art for additional compositions and methods permitting the efficient production of AAV and recombinant AAV viruses for use as vectors for somatic gene therapy without the inefficiency, contamination and purification problems present in the methods previously described.

SUMMARY OF THE INVENTION

The present invention allows for the efficient production of rAAV containing a desired transgene DNA. Once the rAAV itself is constructed, this invention efficiently amplifies the rAAV to yield greater numbers. Particularly, the present invention provides both compositions and methods which enable the production of a rAAV without the need for a helper adenovirus, and without the problem of homologous recombination which produces contaminating re-assembled wt AAV during rAAV production.

The present invention is based on the discovery that contrary to the reported prior art, rAAV production requires the presence of only two adenovirus genes, E1 (i.e., E1a and E1b) and E2a. As used throughout the specification, the term "E1" refers to both E1a and E1b. Thus, "E1 gene product" refers to both the E1a and E1b gene products and "E1 gene" or "E1 gene sequence" refers to both the E1a and E1b genes or gene sequences. The term "E1a" refers specifically to the E1a gene, gene sequences or gene product, and the term "E1b" refers specifically to the E1b gene, gene sequences or gene product. By providing to the host cell only those adenovirus genes which are essential to the production of rAAV, the prior art problem of homologous recombination between the cis plasmid and the helper virus resulting in the reformation of wt helper virus is completely avoided due to the absence of other Ad genes which would be necessary for such recombination to take place. Thus, the only virus produced by the method of this invention is rAAV. The inventors have thereby provided a novel method and host cell for producing rAAV without the need for use of any additional virus, i.e., wildtype or replication-deficient adenovirus helper. This method simplifies the production process for rAAV by eliminating the need for a purification step. Such a purification step is currently required by the rAAV production methods of the prior art in order to separate rAAV from either wtAAV helper virus or any other adenovirus which is formed in the cell, or any virus used to produce the rAAV by homologous recombination.

The rAAV produced by the present method may carry therapeutic transgenes or marker transgenes, and are particularly useful in transferring such transgenes to a host cell or tissue. These rAAV are useful as research reagents, as tools for the recombinant production of a transgene product in vitro, and as therapeutic reagents in gene therapy contexts.

The present invention provides a mammalian host cell containing (1) a transgene flanked by AAV inverse terminal repeats (ITRs) and under the control of regulatory sequences directing expression thereof;
(2) an AAV rep sequence and an AAV cap sequence under the control of regulatory sequences directing expression thereof; and
(3) the minimum adenoviral DNA required to express an E1a gene product, an E1b gene product, and an E2a gene product.

The adenovirus gene products may be transiently produced in the host cell, e.g., where the respective genes are delivered in a transfecting plasmid. Alternatively, they may be stably expressed in the host cell, e.g., where the respective genes are present in the host cell as an episome, or are integrated into the host cell's chromosomes. In one embodiment of the present invention, the AAV rep and cap sequences are transiently expressed in the host cell. In another embodiment, at least one of the E1 and E2a adenoviral genes are transiently expressed in the host cell. Alternatively, in a further embodiment of the present invention, the AAV rep and cap sequences are stably expressed in the host cell. In another embodiment, both the AAV rep and cap sequences and the adenoviral DNA sequences are transiently expressed in the host cell. In another embodiment, at least one, and preferably more, of the E1 and E2a adenoviral genes is stably expressed in the cell. In yet another embodiment, both the AAV rep and cap sequences and the adenoviral DNA are stably expressed in the host cell.

Each of the adenoviral genes may be regulated by an inducible promoter, a constitutive promoter or its native adenoviral promoter. In one embodiment of this invention, the adenoviral DNA encoding at least one of the adenovirus E1a, E1b, and E2a gene products under the regulatory control of an inducible promoter. In another embodiment, the E1 DNA, comprising the E1a and E1b gene products, and the E2a DNA are placed under the control of different inducible promoters. In another embodiment, at least one of the adenoviral E1a, E1b and E2a gene products is placed under the control of a constitutive promoter. In another embodiment, at least one of the adenoviral E1a, E1b or E2a gene products is placed under the control of its native promoter. In a preferred embodiment, the E1 DNA is placed under the control of an inducible promoter and the E2a DNA is placed under the control of its native adenoviral promoter.

The E1a, E1b and E2a genes may be coordinately regulated or may be regulated independently of each other. In one embodiment of this invention, the expression of each of the E1 and E2a gene products is not dependent upon the level of expression of the other adenoviral gene products. In another embodiment of the invention, the expression of at least one of the E1 and E2a gene products is dependent, and therefore, coordinately regulated by expression of one of the adenoviral gene products. In a preferred embodiment, the expression of the E2a gene product is regulated by expression of the E1 gene product.

In a further aspect, the present invention provides a method for producing recombinant adeno-associated virus in the absence of contaminating helper virus or wild-type virus. The method involves isolating a rAAV from the cultured host cells, wherein the cultured cells contain the rAAV expressing the transgene but do not contain contaminating helper virus or wildtype AAV. This method may also include culturing a host cell containing a transgene flanked by AAV ITRs and under the control of regulatory sequences directing expression thereof, an AAV rep gene sequence and an AAV cap gene sequence, in the presence of the minimum adenoviral DNA needed to permit expression of an E1a gene product, an E1b gene product, and an E2a gene product. This method obviates purification steps because there is no helper virus used, nor is there sufficient adenovirus sequence in the host cell to permit homologous recombination to a contaminating wt virus.

Other aspects and advantages of the present invention are described further in the following detailed description of the preferred embodiments thereof.

DETAILED DESCRIPTION OF THE INVENTION

I. Packaging Cell of the Invention

Figure 1:
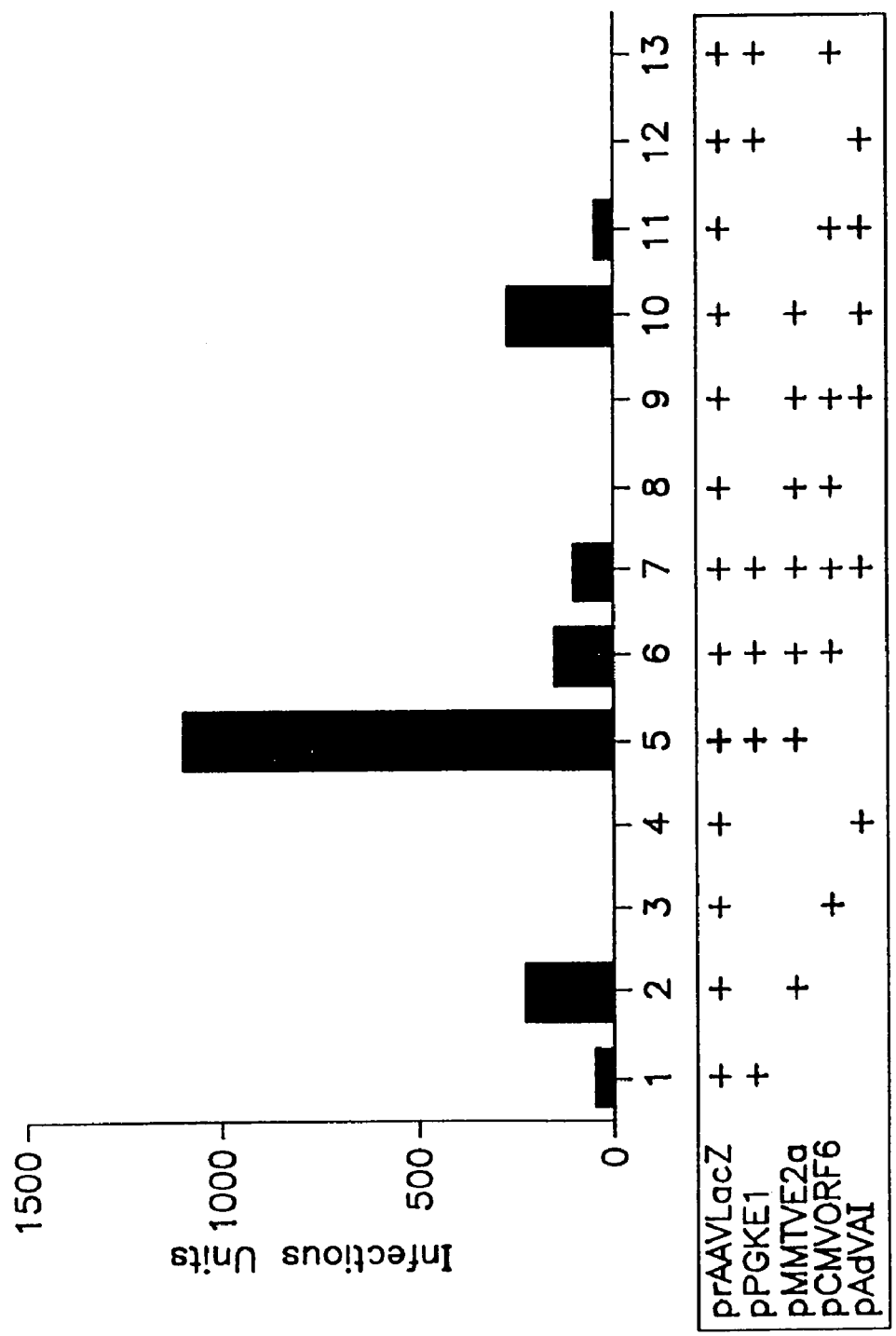
FIG. 1 is a bar graph which plots infectious units (IU) of rAAV produced in the presence of various combinations of adenovirus helper genes provided by plasmids prAAVLacZ (also known as prAAVCMVLacZ), pPGKE1, pMMTVE2a, pCMVORF6, and pAdVAI in B-50 cells. The plasmids used are marked by "+" signs under the X axis and are described in detail in Example 1.

The present invention provides a mammalian host cell containing a transgene flanked by AAV ITRs under the control of regulatory sequences directing expression thereof, an AAV rep sequence and an AAV cap sequence under the control of regulatory sequences directing expression thereof, and the minimum adenoviral DNA required to express an E1a gene product, an E1b gene product, and an E2a gene product.

A. The Transgene

According to the present invention, the host cell contains an engineered nucleic acid molecule which comprises a desired transgene, a promoter, and other regulatory elements which control and direct expression of the transgene in a host cell, flanked by AAV sequences. The transgene sequence is a nucleic acid sequence, heterologous to the AAV sequence, which encodes a polypeptide or protein of interest. The composition of the transgene sequence depends upon the intended use for the resulting rAAV. For example, one type of transgene sequence comprises a reporter or marker sequence, which upon expression produces a detectable signal. Such reporter or marker sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed to them exist or can be made routinely, and fusion proteins comprising a membrane bound protein appropriately fused to an antigen tag domain from, among others, hemagglutinin or Myc.

These sequences, when associated with regulatory elements which drive their expression, provide signals detectable by conventional means, including enzymatic, radiographic, colorimetric, fluorescence or other spectrographic assays, fluorescent activated cell sorting assay and immunological assays, including ELISA, RIA and immunohistochemistry. For example, where the transgene is the LacZ gene, the presence of rAAV is detected by assays for beta-galactosidase activity. Similarly, where the transgene is luciferase, rAAV may be measured by light production in a luminometer.

However, desirably, the transgene is a non-marker gene which can be delivered to a cell or an animal via the rAAV produced by this method. The transgene may be selected from a wide variety of gene products useful in biology and medicine, such as proteins, antisense nucleic acids (e.g., RNAs), or catalytic RNAs. The invention may be used to correct or ameliorate gene deficiencies, wherein normal genes are expressed but at less than normal levels, and may also be used to correct or ameliorate genetic defects wherein a functional gene product is not expressed. A preferred type of transgene sequence is a therapeutic gene which expresses a desired gene product in a host cell. These therapeutic nucleic acid sequences typically encode products which, upon expression, are able to correct or complement an inherited or non-inherited genetic defect, or treat an epigenetic disorder or disease. However, the selected transgene may encode any product desirable for study. The selection of the transgene sequence is not a limitation of this invention. Choice of a transgene sequence is within the skill of the artisan in accordance with the teachings of this application.

The invention also includes methods of producing rAAV which can be used to correct or ameliorate a gene defect caused by a multi-subunit protein. In certain situations, a different transgene may be used to encode each subunit of the protein. This is desirable when the size of the DNA encoding the protein subunit is large, e.g., for an immunoglobulin or the platelet-derived growth factor receptor. In order for the cell to produce the multi-subunit protein, a cell would be infected with rAAV containing each of the different subunits. Alternatively, different subunits of a protein may be encoded by the same transgene. In this case, a single transgene would include the DNA encoding each of the subunits, with the DNA for each subunit separated by an internal ribosome entry site (IRES). This is desirable when the size of the DNA encoding each of the subunits is small, such that the total of the DNA encoding the subunits and the IRES is less than five kilobases.

Useful gene products include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factors (CTGF), basic fibroblast growth factor (bFGF), acidic fibroblast growth factor (aFGF), epidermal growth factor (EGF), transforming growth factor α (TGFα), platelet-derived growth factor (PDGF), insulin-like growth factors I and II (IGF-I and IGF-II), any one of the transforming growth factor β (TGFβ) superfamily comprising TGFβ, activins, inhibins, or any of the bone morphogenic proteins (BMP) BMPs 1–15, any one of the heregulin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful gene products include proteins that regulate the immune system including, without limitation, cytokines and lymphokines such as thrombopoietin (TPO), interleukins (IL) IL-1α, IL-1β, IL-2, IL-3, IL-4, IL-5, IL-6, IL-7, IL-8, IL-9, IL-10, IL-11, IL-12, IL-13, IL-14, IL-15, IL-16, and IL-17, monocyte chemoattractant protein (MCP-1), leukemia inhibitory factor (LIF), granulocyte-macrophage colony stimulating factor (GM-CSF), Fas ligand, tumor necrosis factors α and β (TNFα and TNFβ), interferons (IFN) IFN-α, IFN-β and IFN-γ, stem cell factor, flk-2/flt3 ligand. Gene products produced by the immune system are also encompassed by this invention. These include, without limitations, immunglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered MHC molecules including single chain MHC molecules. Use gene products also include complement regulatory proteins such as complement regulatory proteins, membrane cofactor protein (MCP), decay accelerating factor (DAF), CR1, CR2 and CD59.

Still other useful gene products include any one of the receptors for the hormones, growth factors, cytokines, lymphokines, regulatory proteins and immune system proteins. The invention encompasses receptors for cholesterol regulation, including the LDL receptor, HDL receptor, VLDL receptor, and the scavenger receptor. The invention also encompasses gene products such as steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP-2, myb, MRG1, CREM, Alx4, FREAC1, NF-κB, members of the leucine zipper family, C2H4 zinc finger proteins, including Zif268, EGR1, EGR2, C6 zinc finger proteins, including the glucocorticoid and estrogen receptors, POU domain proteins, exemplified by Pit1, homeodomain proteins, including HOX-1, basic helix-loop-helix proteins, including myc, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor 1 (IRF-1), Wilms tumor protein, ETS-binding protein, STAT, GATA-box binding proteins, e.g., GATA-3, and the forkhead family of winged helix proteins.

Other useful gene products include carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione beta-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, beta-glucosidase, pyruvate carboxylase, hepatic phosphorylase, phosphorylase kinase, glycine decarboxylase (also referred to as P-protein), H-protein, T-protein, Menkes disease protein, tumor suppressors (e.g., p53), cystic fibrosis transmembrane regulator (CFTR), and the product of Wilson's disease gene PWD.

Other useful transgenes include non-naturally occurring polypeptides, such as chimeric or hybrid polypeptides or polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a gene.

Design of the transgene for expression in mammalian cells and hosts should include appropriate sequences that are operably linked to the gene of interest to promote its expression. "Operably linked" sequences include both expression control sequences that are contiguous with the gene of interest and expression control sequences that act in trans or at a distance to control the gene of interest. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. A great number of expression control sequences—native, constitutive, inducible and/or tissue-specific—are known in the art and may be utilized to drive expression of the transgene, depending upon the type of expression desired. For eukaryotic cells, expression control sequences typically include a promoter, an enhancer, such as one derived from an immunoglobulin gene, SV40, cytomegalovirus, etc., and a polyadenylation sequence which may include splice donor and acceptor sites. The polyadenylation sequence generally is inserted following the transgene sequences and before the 3' AAV ITR sequence. A transgene-carrying molecule useful in the present invention may also contain an intron, desirably located between the promoter/enhancer sequence and the transgene. One possible intron sequence is also derived from SV-40, and is referred to as the SV-40 T intron sequence. Another vector element that may be used is an internal ribosome entry site (IRES). An IRES sequence is used to produce more than one polypeptide from a single gene transcript. An IRES sequence would be used to produce a proteins that contain more than one polypeptide chains. Selection of these and other common vector elements are conventional and many such sequences are available [see, e.g., Sambrook et al, and references cited therein at, for example, pages 3.18–3.26 and 16.17–16.27 and Ausubel et al., *Current Protocols in Molecular Biology*, John Wiley & Sons, New York, 1989].

In one embodiment, high-level constitutive expression will be desired. Examples of such promoters include, without limitation, the retroviral Rous sarcoma virus (RSV) LTR promoter/enhancer, the cytomegalovirus (CMV) immediate early promoter/enhancer [see, e.g., Boshart et al, *Cell,* 41: 521–530 (1985)], the SV40 promoter, the dihydrofolate reductase promoter, the cytoplasmic β-actin promoter and the phosphoglycerol kinase (PGK) promoter.

In another embodiment, inducible promoters may be desired. Inducible promoters are those which are regulated by exogenously supplied compounds, including without limitation, the zinc-inducible sheep metallothionine (MT) promoter; the dexamethasone (Dex)-inducible mouse mammary tumor virus (MMTV) promoter; the T7 polymerase promoter system [WO 98/10088]; the ecdysone insect promoter [No et al, *Proc. Natl. Acad. Sci. USA,* 93: 3346–3351 (1996)]; the tetracycline-repressible system [Gossen et al, *Proc. Natl. Acad. Sci. USA,* 89: 5547–5551 (1992)]; the tetracycline-inducible system [Gossen et al., *Science,* 268: 1766–1769 (1995); see also Harvey et al., *Curr. Opin. Chem. Biol.,* 2: 512–518 (1998)]; the RU486-inducible system [Wang et al., *Nat. Biotech.,* 15: 239–243 (1997) and Wang et al., *Gene Ther.,* 4: 432–441 (1997)]; and the rapamycin-inducible system [Magari et al. *J. Clin. Invest.,* 100: 2865–2872 (1997)]. Other types of inducible promoters which may be useful in this context are those which are regulated by a specific physiological state, e.g., temperature, acute phase, or in replicating cells only. In a preferred embodiment, the transgene is under the control of the P5 native AAV promoter.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the transgene includes transgene operably linked to a tissue-specific promoter. For instance, if expression in skeletal muscle is desired, a promoter active in muscle should be used. These include the promoters from genes encoding skeletal α-actin, myosin light chain 2A, dystrophin, muscle creatine kinase, as well as synthetic muscle promoters with activities higher than naturally-occurring promoters [see Li et al., *Nat. Biotech.,* 17: 241–245 (1999)]. Examples of promoters that are tissue-specific are known for liver [albumin, Miyatake et al. *J. Virol.,* 71: 5124–32 (1997); hepatitis B virus core promoter, Sandig et al., *Gene Ther.,* 3: 1002–9 (1996); alpha-fetoprotein (AFP), Arbuthnot et al., *Hum. Gene Ther.* 7: 1503–14 (1996)], bone [osteocalcin, Stein et al., *Mol. Biol. Rep.,* 24: 185–96 (1997); bone sialoprotein, Chen et al., *J. Bone Miner. Res.,* 11: 654–64 (1996)], lymphocytes [CD2, Hansal et al., *J. Immunol.,* 161: 1063–8 (1998); immunoglobulin heavy chain; T cell receptor α chain], neuronal [neuron-specific enolase (NSE) promoter, Andersen et al. *Cell. Mol. Neurobiol.,* 13: 503–15 (1993); neurofilament light-chain gene, Piccioli et al., *Proc. Natl. Acad. Sci. USA,* 88: 5611–5 (1991); the neuron-specific vgf gene, Piccioli et al., *Neuron,* 15: 373–84 (1995); among others.

Of course, not all vectors and expression control sequences will function equally well to express all of the transgenes of this invention. However, one of skill in the art may make a selection among these expression control sequences without departing from the scope of this invention. Suitable promoter/enhancer sequences may be selected by one of skill in the art using the guidance provided by this application. Such selection is a routine matter and is not a limitation of the molecule or construct. For instance, one may select one or more expression control sequences, operably link the sequence to a transgene of interest, and insert the "minigene" comprising the expression control sequence and the transgene into an AAV vector. After following one of the methods for packaging the rAAV taught in this specification, or as taught in the art, one may infect suitable cells in vitro or in vivo. The number of copies of the transgene in the cell may be monitored by Southern blotting or quantitative PCR; the level of RNA expression may be monitored by Northern blotting or quantitative RT-PCR; and the level of protein expression may be monitored by Western blotting, immunohistochemistry, ELISA, RIA, or tests of the transgene's gene product's biological activity. Thus, one may easily assay whether a particular expression control sequence is suitable for a specific transgene, and choose the expression control sequence most appropriate for expression of the desired transgene.

The AAV sequences employed are preferably the cis-acting 5' and 3' inverted terminal repeat sequences [See, e.g., B. J. Carter, in "Handbook of Parvoviruses", ed., P. Tijsser, CRC Press, pp. 155–168 (1990)]. The ITR sequences are about 145 bp in length. Preferably, substantially the entire sequences encoding the ITRs are used in the molecule, although some degree of minor modification of these sequences is permissible. The ability to modify these ITR sequences is within the skill of the art. [See, e.g., texts such as Sambrook et al, "Molecular Cloning. A Laboratory Manual", 2d ed., Cold Spring Harbor Laboratory, New York (1989); Carter et al, cited above; and K. Fisher et al., *J. Virol.* 70: 520–532 (1996)]. An example of such a molecule employed in the present invention is a "cis-acting" plasmid containing the transgene, in which the selected transgene sequence and associated regulatory elements are flanked by the 5' and 3' AAV ITR sequences.

The AAV ITR sequences may be obtained from any known AAV, including presently identified human AAV types. Similarly, AAVs known to infect other animals may also provide these ITRs employed in the molecules or constructs of this invention. For example, the ITRs may be provided by AAV type 1, AAV type 2, AAV type 3, AAV type 4, AAV type 5, AAV 6, other AAV serotypes or densovirus. A variety of AAV strains are available from the American Type Culture Collection or are available by request from a variety of commercial and institutional sources. In the following exemplary embodiments an AAV-2 is used for convenience. However, the selection of the species and serotype of AAV that provides these sequences is within the skill of the artisan according to the teachings of this application and does not limit the following invention.

The nucleic acid molecule carrying the AAV ITRs flanking the transgene and regulatory sequences (e.g., promoters, polyA sequences, etc.) may be in any form which transfers these components to the host cell. The nucleic acid molecule comprising the AAV ITRs, transgene and regulatory sequences may be contained within a vector. A "vector" includes, without limitation, any genetic element, such as a plasmid, phage, transposon, cosmid, chromosome, virus, virion, etc., which can transfer gene sequences to a cell. Thus, the term includes cloning and expression vehicles, as well as viral vectors. Transformation and other methods of introducing nucleic acids into a host cell (e.g., transfection, electroporation, liposome delivery, membrane fusion techniques, high velocity DNA-coated pellets, viral infection and protoplast fusion) can be accomplished by a variety of methods which are well known in the art (see, for instance, Ausubel et al. and Sambrook et al., supra). Mammalian cells are transformed or transfected with an expression vector, such as a plasmid, a cosmid, or the like, wherein the expression vector comprises the DNA of interest. Introduction into mammalian cells can be achieved using a variety of plasmids, including pcDNA, pSV2, pBC12BI, and p91023, as well as lytic virus vectors (e.g., vaccinia virus), episomal virus vectors (e.g., bovine papillomavirus), and retroviral vectors (e.g., murine retroviruses).

In one preferred embodiment, the rAAV transgene comprising the transgene is contained within a plasmid vector. The plasmids of this invention may be engineered such that they are suitable for replication and, optionally, integration in prokaryotic cells, mammalian cells, or both. Shuttle vectors comprise sequences permitting replication of the cassette in both eukaryotes and prokaryotes, and selection markers for both prokaryotic and eukaryotic systems. See, e.g., Sambrook and Ausubel, supra. Selectable markers or reporter genes include sequences encoding geneticin, hygromycin or purimycin resistance, among others. It may also contain certain selectable reporters or marker genes that can be used to grow the vector in bacterial cells, such as ampicillin resistance. Other components of the plasmid may include an origin of replication and an amplicon, such as the amplicon system, employing the Epstein Barr virus nuclear antigen, for example, the vector components in pCEP4 (Invitrogen). See, also, J. Horvath et al, Virology, 184: 141–148 (1991). This amplicon system or similar amplicon components permit high copy episomal replication in the cells. Preferably, this nucleic acid molecule is transfected into the cell, where it may exist transiently or preferably stably as an episome. Alternatively, the entire molecule, but at least the transgene and regulatory sequences, may be stably integrated into a chromosome of the host cell.

Alternatively, the cells may be infected by a viral expression vector comprising the DNA or RNA of interest. In a preferred embodiment, the rAAV construct comprising the transgene is contained within a hybrid adenovirus/AAV vector. The hybrid vector comprises selected portions of an adenovirus sequence, 5' and 3' AAV ITR sequences which flank a selected transgene under the control of a selected promoter and other conventional vector regulatory components. See U.S. Pat. Nos. 5,856,152 and 5,871,982. The adenovirus sequences may be derived from a wildtype adenovirus or a mutant adenovirus. In the hybrid vector construct, the AAV sequences are flanked by the selected adenoviral sequences. The minimum adenovirus sequences employed are the cis-acting 5' and 3' inverted terminal repeat (ITR) sequences of an adenovirus (which function as origins of replication) and the native 5' packaging/enhancer domain, that contains sequences necessary for packaging linear Ad genomes and enhancer elements for the E1 promoter. The 5' and 3' AAV ITR sequences themselves flank a selected transgene sequence and its associated regulatory element. The deleted gene products can be supplied in the hybrid viral production process by a selected packaging cell or by the hybrid vector itself The deleted gene products include E1, E2a, E4ORF6 and VAI RNA. In a preferred embodiment, the selected packaging cell contains E1 and E2a. Once the hybrid virus or trans-infection particle is taken up by a cell, the AAV ITR flanked transgene must be rescued from the parental adenovirus backbone by supplying the infected cell with an AAV rep gene, which preferably is present in the host packaging cell. The recombinant AAV genome is packaged by supplying the infected cell with an AAV cap gene, which is preferably present in the host packaging cell.

The engineering methods used to construct any embodiment of this invention are known to those with skill in nucleic acid manipulation and include genetic engineering, recombinant engineering, and synthetic techniques. See, e.g., Sambrook et al, and Ausubel et al., cited above; and International Patent Application No. WO95/13598.

In the examples below, an exemplary transgene-containing molecule is the cis-acting plasmid referred to as prAAVCMVLacZ, described in Example 1.

B. The AAV rep and cap Sequences

The host cell according to the present invention also contains an AAV rep sequence and an AAV cap gene sequence, preferably under the regulatory control of a promoter sequence. The AAV rep and cap sequences are obtained from an AAV source as identified above. The AAV rep and cap sequences may be introduced into the host cell in any manner known to one in the art as described above, including, without limitation, transfection, electroporation, liposome delivery, membrane fusion techniques, high velocity DNA-coated pellets, viral infection and protoplast fusion. In one embodiment, the rep and cap sequences may be transfected into the host cell by one or more nucleic acid molecules and exist stably in the cell as an episome. In another embodiment, the rep and cap sequences are stably integrated into the genome of the cell. A stable host cell line that contains rep and cap is B-50, described in PCT/US98/19463. Another embodiment has the rep and cap sequences transiently expressed in the host cell. For example, a useful nucleic acid molecule for such transfection comprises, from 5' to 3', a promoter, an optional spacer interposed between the promoter and the start site of the rep gene sequence, an AAV rep gene sequence, and an AAV cap gene sequence.

The rep and cap sequences, along with their expression control sequences, may be supplied on a single vector, or each sequence may be supplied on its own vector. Preferably, the rep and cap sequences are supplied on the same vector. Alternatively, the rep and cap sequences may be supplied on a vector that contains other DNA sequences that are to be introduced into the host cells. For instance, the vector may contain the rAAV construct comprising the transgene. The vector may comprise one or more of the genes encoding the adenoviral proteins E1, E2a, and E4ORF6, and the gene for VAI RNA. A preferred embodiment of this vector contains the rep and cap genes and the E1 and E2a genes. The vector may also comprise the rep and cap sequences, the rAAV construct and the adenoviral genes. A preferred embodiment of the vector contains the rep and cap sequences, the rAAV construct and the adenoviral genes E1 and E2a.

Preferably, the promoter used in this construct may be any of the constitutive, inducible or native promoters known to one of skill in the art or as discussed above. In a preferred embodiment, an AAV P5 promoter sequence is employed. While it may be obtained from any of the above-mentioned AAV sources, the parvovirus P5 promoter is preferably homologous to the AAV serotype which provides the rep and cap gene sequences. Alternatively, the promoter may be a P5 promoter from another AAV type than that which provides the rep and cap sequences. AAVs known to infect other humans or other animals may also provide the P5 promoter. The selection of the AAV to provide any of these sequences does not limit the invention.

In another preferred embodiment, the promoter for rep is an inducible promoter. As discussed above, inducible promoters include, without limitation, the metallothionine (MT) promoter; the dexamethasone (Dex)-inducible mouse mammary tumor virus (MMTV) promoter; the T7 polymerase promoter system; the ecdysone insect promoter; the tetracycline-repressible system; the tetracycline-inducible system; the RU486-inducible system; and the rapamycin-inducible system. One preferred promoter for rep expression is the T7 promoter. The vector comprising the rep gene regulated by the T7 promoter and the cap gene, is transfected or transformed into a cell which either constitutively or inducibly expresses the T7 polymerase. See WO 98/10088, published Mar. 12, 1998.

The spacer is an optional element in the design of the vector. The spacer is a DNA sequence interposed between the promoter and the rep gene ATG start site. The spacer may have any desired design; that is, it may be a random sequence of nucleotides, or alternatively, it may encode a gene product, such as a marker gene. The spacer may contain genes which typically incorporate start/stop and polyA sites. The spacer may be a non-coding DNA sequence from a prokaryote or eukaryote, a repetitive non-coding sequence, a coding sequence without transcriptional controls or coding sequences with transcriptional controls. Two exemplary sources of spacer sequences are the λ phage ladder sequences or yeast ladder sequences, which are available commercially, e.g., from Gibco or Invitrogen, among others. The spacer may be of any size sufficient to reduce expression of the rep78 and rep68 gene products, leaving the rep52, rep40 and cap gene products expressed at normal levels. The length of the spacer may therefore range from about 10 bp to about 10.0 kbp, preferably in the range of about 100 bp to about 8.0 kbp. To reduce the possibility of recombination, the spacer is preferably less than 2 kbp in length; however, the invention is not so limited.

Exemplary molecules providing the AAV rep and cap proteins are described in the examples, e.g., pMT-Rep/Cap, pP5-Rep/Cap and pMMTV-Rep/Cap. These plasmids each contain a neomycin selective marker gene and express the AAV rep/cap genes driven by either their native P5 promoter (pP5-Rep/Cap), the zinc-inducible sheep metallothionine promoter (pMTRep/Cap), or the dexamethasone (Dex)-inducible mouse mammary tumor virus (MMTV) promoter (pMMTV-Rep/Cap). Although these proteins may be provided to the cell by various means, exemplary methods of the invention include use of various plasmids. For construction of plasmid pMT-Rep/Cap, the ORF6 sequence was removed from a pMTE4ORF6 plasmid [G. P. Gao et al, *J. Virol.*, 70: 8934–8943 (1996)] by BamHI digestion and replaced with a 4.1 kb rep/cap fragment which was prepared by PCR amplification using pSub201 plasmid [Samulski, R. J. et al., *J. Virol.*, 63: 3822–3828 (1989)] as a template. Plasmid pMMTV-Rep/Cap was constructed in the same way as pMT-Rep/Cap, except that a pMMTVE4ORF6 plasmid [Gao et al, cited above] was used as the vector backbone. For construction of P5-Rep/Cap, the MT promoter and ORF6 sequences were removed from a pMTE4ORF6 plasmid [G. P. Gao et al, *J. Virol.*, 70: 8934–8943 (1996)] by EcoRI/BamHI digestion and replaced with a 4.3 kb P5-Rep/Cap fragment which was isolated from a pSub201 plasmid [Samulski, R. J. Et al, *J. Virol.* 63: 3822–3828 (1989)] by XbaI digestion. Plasmid construction involved conventional genetic engineering methods, such as those described in Sambrook et al, cited above. All of the above-cited references are incorporated by reference herein.

A variety of other plasmid constructs providing the rep and cap proteins are known in the art and may be employed in the host cell of the invention. For example, the rep/cap constructs may omit the spacer between the promoter and the rep/cap genes referred to in the construct described above. Other constructs of the art, such as that described in U.S. Pat. No. 5,622,856, which places the P5 promoter 3' to the rep/cap genes, may also be employed in this context.

The molecule providing the rep and cap proteins may be in any form which transfers these components to the host cell. As exemplified herein, this molecule is preferably in the form of a plasmid, which may contain other non-viral sequences, such as those for marker genes. This molecule does not contain the AAV ITRs and generally does not contain the AAV packaging sequences. To avoid the occurrence of homologous recombination, other virus sequences, particularly those of adenovirus, are avoided in this plasmid. This plasmid is desirably constructed so that it may be stably transfected into a cell.

Although the molecule providing rep and cap may exist in the host cell transiently (i.e., through transfection), it is preferred that the rep/cap proteins and the promoter controlling their expression be stably expressed in the host cell, e.g., as an episome or by integration into the chromosome of the host cell.

The methods employed for constructing embodiments of this invention are conventional genetic engineering or recombinant engineering techniques such as those described in the references above. While this specification provides illustrative examples of specific constructs, using the information provided herein, one of skill in the art may select and design other suitable constructs, using a choice of spacers, P5 promoters, and other elements, including at least one translational start and stop signal, and the optional addition of polyadenylation sites.

In another embodiment of this invention, the rep and cap proteins may be provided stably by a host cell, such as the B-50 cell, as described in detail below.

C. The Adenovirus E1a, E1b and E2a Genes

The host cell according to this invention further contains the minimum adenoviral DNA which is sufficient to express an E1a gene product, an E1b gene product and an E2a gene product. The host cell may contain other adenoviral genes such as E4ORF6 and/or VAI RNA, but these genes are not required. In a preferred embodiment, no other adenovirus genes or gene functions are supplied by the host cell.

The DNA sequences encoding the adenovirus E1 and E2a genes useful in this invention may be selected from among any known adenovirus type, including the presently identified 46 human types [see, e.g., Horwitz, cited above and American Type Culture Collection]. Similarly, adenoviruses known to infect other animals may supply the gene sequences. The selection of the adenovirus type for each E1 and E2a gene sequence does not limit this invention. The sequences for a number of adenovirus serotypes, including that of serotype Ad5, are available from Genbank. A variety of adenovirus strains are available from the American Type Culture Collection (ATCC), Manassas, Va., or are available by request from a variety of commercial and institutional sources. Any one or more of human adenoviruses Types 1 to 46 may supply any of the adenoviral sequences, including E1 and E2a. In the following exemplary embodiment the E1 and E2a gene sequences are those from adenovirus serotype 5 (Ad5).

By "adenoviral DNA which expresses the E1a gene product", it is meant any adenovirus gene encoding E1a or any functional E1a portion. Similarly included are any alleles or other modifications of the E1a gene or functional portion thereof. Such modifications may be deliberately introduced by resort to conventional genetic engineering or mutagenic techniques to enhance the E1a function in some manner, as well as naturally occurring allelic variants thereof.

By "adenoviral DNA which expresses the E1b gene product", it is meant any adenovirus gene encoding E1b or any functional E1b portion thereof. Similarly included are any alleles or other modifications of the E1b gene or functional portion. Such modifications may be deliberately introduced by resort to conventional genetic engineering or mutagenic techniques to enhance the E1b function in some manner, as well as naturally occurring allelic variants thereof.

By "adenoviral DNA which expresses the E2a gene product", it is meant any adenovirus gene encoding E2a or any functional E2a portion. Similarly included in that definition are any alleles or other modifications of the E2a gene or functional portion thereof. Such modifications may be deliberately introduced by resort to conventional genetic engineering or mutagenic techniques to enhance the E2a function in some manner, as well as naturally occurring allelic variants thereof. Such modifications and methods for manipulating DNA to achieve these adenovirus gene functions are known to those of skill in the art.

The E1a, E1b, and E2a gene products, as well as any other desired adenoviral gene products, can be provided using any means that allows their expression in a cell. Each of the genes may be on a separate vector, or one or more genes may be on the same vector. The vector may be any vector known in the art or disclosed above, including plasmids, cosmids and viruses. Introduction into the host cell of the vector comprising the gene product may be achieved by any means known in the art or as disclosed above, including transfection, infection, among others. The adenoviral gene products, especially E1 and E2a, may be stably integrated into the genome of the host cell, stably expressed as an episome, or expressed transiently. The genes may all be expressed transiently, on an episome or stably integrated, or some of the genes may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously-added factors, for example.

The E1 and E2a promoters may be identical or may be different. A variety of promoters may be used to drive expression of the adenovirus genes in the host cells according to the above embodiments and include constitutive, inducible and native promoters. Any promoter allowing expression of E1a, E1b and E2a may be employed, and the proteins may be expressed from the same or from different promoters. Each promoter may be one which is naturally associated with the 5' flanking region of the adenovirus gene or may be a heterologous promoter.

In one embodiment of the invention, the E1 gene product may be provided to the cell in the form of a nucleic acid sequence encoding both E1a and E1b. The nucleic acid comprising E1 may be, without limitation, a plasmid, a cosmid, a hybrid adenovirus/AAV vector, e.g., as described in U.S. Pat. No. 5,856,152, a retrovirus, or another type of virus. The expression of the E1a gene may be directed by either an inducible or constitutive promoter. Once E1a expression is initiated by its promoter, E1a production then activates the native E1b promoter, resulting in the expression of E1b. In one embodiment, the molecule carrying the E1 gene is a plasmid which can exist in a transfected host cell transiently. Preferably, the nucleic acid sequence or plasmid stably exists in the host cell as an episome, or is integrated into the chromosomes of the host cell, so that E1a and E1b gene products are produced stably by the host cell.

In one embodiment, the E1a gene (and subsequently the E1b gene) is expressed under the control of a constitutive promoter, including, without limitation, the RSV LTR promoter/enhancer, the CMV immediate early promoter/enhancer, the SV40 promoter, the dihydrofolate reductase promoter, the cytoplasmic β-actin promoter and the phosphoglycerol kinase (PGK) promoter.

In a preferred embodiment, an inducible promoter is employed to express the E1 gene products, so as to control the amount and timing of the cell's production of the E1a and E1b gene products, which can be toxic to the cell upon excessive accumulation [see, e.g., William S. M. Wold, *J. Cell Biochem.*, 53: 329–335 (1993); J. Nevins, Current Opinion in Genetics and Development, 4: 130–134 (1994); E. Harrington et al, Current Opinion in Genetics and Development, 4: 120–129 (1994); G. Evan et al, Current Opinion in Cell Biology, 7: 825–834 (1995); J. Nevins, Science, 258:424 (1992)]. Inducible promoters include those known in the art and those discussed above including, without limitation, the zinc-inducible sheep metallothionine (MT) promoter; the dexamethasone (Dex)-inducible mouse mammary tumor virus (MMTV) promoter; the T7 promoter; the ecdysone insect promoter; the tetracycline-repressible system; the tetracycline-inducible system; the RU486-inducible system; and the rapamycin-inducible system. Any type of inducible promoter which is tightly regulated and which provides for high-level expression of E1 may be used. Other types of inducible promoters which may be useful in this context are those which are regulated by a specific physiological state, e.g., temperature, acute phase, a particularly differentiation state of the cell, or in replicating cells only.

According to the present invention, the adenovirus DNA which expresses the E2a gene product may be provided to the host cell in the form of a nucleic acid sequence which also includes a promoter directing the expression of the E2a gene product and other optional regulatory components. As described above, the nucleic acid molecule may be provided in any form to the cell including transfection or infection, and may exist in the cell transiently, or preferably stably as an episome or integrated into the cell's chromosomes. The promoter for E2a may be a constitutive, inducible or native promoter, as discussed above.

While the promoter in control of the expression of the E2a gene product may be a constitutive promoter in certain embodiments, in one preferred embodiment, the promoter be an inducible promoter so as to control the amount and timing of E2a gene product generation (which is toxic to the cell upon over-accumulation [D. Brough et al, *Virology*, 190: 624–634 (1992) and D. Klessig et al, *Virus Res.*, 1: 169–188 (1984)]) relative to the production of the E1 gene products. See FIG. 2 and Example 2. One preferred embodiment provides that the promoter directing the production of E2a be a different inducible promoter from that directing the expression of E1a and E1b, and be inducible by exposure to a different inducing agent than that used for the E1 inducible promoter.

Where each inducible promoter in control of expression of E1 and E2a gene products is responsive to a different inducing agent, the timing, and therefore the ratio, of E1 and E2a gene products in the host cell may be controlled by delivery of the appropriate inducing agent. Such control of the ratio of E1 gene product to E2a gene product in the cell line can enhance the production rate of rAAV produced in the cell line. See, e.g., Examples 2 and 3.

In another preferred embodiment, the promoter for E2a is its native promoter. Once E1 expression is initiated by its promoter, E1 then activates the native E2a promoter, resulting in expression of E2a. In this manner, the adenoviral gene sequences may be controlled by only a single promoter, that for E1a. Once E1a is expressed, it activates expression of E1b and E2a. In addition, E1 also activates expression of other adenoviral genes, such as E4ORF6 and VAI RNA via their native promoters. Therefore, this system provides a simplified method of producing those adenoviral genes required for rAAV production in a cell system. The selection of the appropriate promoters for the host cells of this invention may be performed by one of skill in the art in accordance with the present invention with reference to factors such as the type of mammalian cell, whether the gene to be expressed is present in the cell transiently or stably as an episome or integrated in the cell, as well as the culture conditions of the cell itself when it is employed to produce recombinant AAV.

D. The Host Cells

The adenoviral gene products can be introduced into the cells by any other methods discussed above, including transfection, electroporation, liposome delivery, membrane fusion techniques, high velocity DNA-coated pellets, viral infection and protoplast fusion.

The mammalian host cell itself may be selected from any mammalian species, such as human cell types, including, without limitation, cells such as A549, WEHI, 3T3, 10T1/2, BHK, MDCK, COS 1, COS 7, BSC 1, BSC 40, BMT 10, VERO, WI38, HeLa, 293 cells (which express functional adenoviral E1), Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc. The requirements for the cell used is that it must not carry any adenovirus gene other than E1 and E2a; it must not contain any other virus gene which could result in homologous recombination of a contaminating virus during the production of rAAV; and it must be capable of transfection of DNA and expression of the transfected DNA. In a preferred embodiment, the host cell is one that has rep and cap stably transfected in the cell, such as the B50 cell line.

As discussed above, this invention includes the following illustrative embodiments:

(a) a cell which transiently expresses the AAV rep and cap genes, the adenovirus E1 and E2a gene products, and the nucleic acid molecule comprising the transgene;

(b) a cell which stably expresses the AAV rep and cap genes carried on an episome or integrated into the chromosomes of the cell, and transiently expresses the adenovirus E1 and E2a gene products and the nucleic acid molecule comprising the transgene;

(c) a cell which stably expresses at least one of the AAV rep and cap genes, and the adenovirus E1 and E2a gene products (or functional fragments thereof), and transiently expresses the nucleic acid molecule comprising the transgene;

(d) a cell which stably expresses the AAV rep gene, the AAV cap gene, the adenovirus E1a gene, E1b gene and E2a gene (or functional fragments thereof) stably as one or more episomes or as integrated DNA, and which transiently expresses the transgene-containing nucleic acid molecule; and (e) a cell which stably expresses the AAV rep and cap genes, the adenovirus E1 and E2a gene products, and the nucleic acid molecule comprising the transgene.

One exemplary host cell of the present invention under option C above is the B-50 cell stably expressing rep and cap, which is transfected with the adenovirus E1 and E2a DNA and the transgene-containing nucleic acid molecule described above. This host cell is described in detail in Example 1 below where B-50 was transfected with prAAVCMVLacZ, pMMTVE2a and pPGKE1. Other stable rep/cap expressing cell lines, such as those described in U.S. Pat. No. 5,658,785, may also be similarly employed.

The preparation of a host cell according to this invention involves techniques such as assembly of selected DNA sequences. This assembly may be accomplished utilizing conventional techniques. Such techniques include cDNA and genomic cloning, which is well known and is described in Sambrook et al. and Ausubel et al., cited above, use of overlapping oligonucleotide sequences of the adenovirus and AAV genomes, combined with polymerase chain reaction, synthetic methods, and any other suitable methods which provide the desired nucleotide sequence.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation, and/or infection by hybrid adenovirus/AAV vectors into cell lines such as the human embryonic kidney cell line HEK 293 (a human kidney cell line containing functional adenovirus E1 genes which provides trans-acting E1 proteins) and the B50 cell lines (a HeLa cell line containing stably integrated rep and cap genes.

II. Method of the Invention

As described above, the various embodiments of the host cells may be employed in another aspect of this invention, i.e., a method for producing recombinant adeno-associated virus in the absence of contaminating helper virus or wild-type virus. This method is accomplished by performing the following steps:

(a) culturing a mammalian host cell containing a transgene flanked by adeno-associated virus inverse terminal repeats under the control of regulatory sequences directing expression thereof, an AAV rep sequence and an AAV cap sequence under the control of regulatory sequences directing expression thereof, and the minimum adenoviral DNA required to express an E1a gene product, an E1b gene product, and an E2a gene product using any of the above-described embodiments of the host cells; and (b) isolating from the cell or cell culture a recombinant AAV which expresses said transgene, in the absence of contaminating helper virus or wildtype AAV.

Conventional techniques employed in this method include cloning of the rAAV viral genomes, and methods of measuring signal generation, and the like. No purification step is needed to detect message or signal or to separate the rAAV from other viruses. Generally, in production, conventional purification techniques such as chloride gradient centrifugation or column chromatography are used to concentrate the rAAV from the cellular proteins in the lysate.

In a preferred embodiment of this method, the adenoviral E1 and E2a gene products are expressed under the control of at least one inducible promoter. Thus, this method further includes the step of contacting the cultured host cells with at least one inducing agent, which controls the expression of at least one of the required adenovirus gene products. See, e.g., Examples 1 and 4 below. Where the host cell contains each adenovirus gene product under control of a different inducible promoter, the method further entails the steps of adding to the host cell culture a first inducing agent for the first inducible promoter and a second inducing agent for the second inducible promoter. This embodiment of the method thus permits cellular expression of the adenoviral E1a and E1b gene products in a desired ratio to the expression of said adenoviral E2a gene product which is optimal for rAAV production in the particular host cell under suitable culture conditions for that cell. See, e.g., Examples 2 and 3 below.

The determination of a suitable ratio of E1 gene products to E2a gene products and the AAV rep/cap products may be accomplished by one of skill in the art, taking account of the cell type, the strength of constitutive and/or inducible promoters used, the amounts of inducer(s) used, and the order or timing of induction of preferred gene products. The optimal ratio which permits the greatest production of rAAV may differ as these factors differ. For example, a 5.2:1 ratio of E1:E2a containing plasmids was found to be the optimal ratio in Example 2 below. See, e.g., FIG. 2. Thus, a certain amount of routine experimentation must be performed to assess the optimal ratio in each instance, as is shown in Examples 2 and 3. For example, where the E1a gene is controlled by a weak or medium strength constitutive promoter, the E2a gene should be controlled by a strong inducible promoter and the inducing agent added early in the culture to obtain a suitable ratio. Where the E1a gene is controlled by an inducible promoter as well as the E2a gene, the two inducing agents may be added in varying amounts and at varying orders of induction to provide the optimal production system for rAAV. However, such optimization experimentation employed to determine preferred amounts and orders is well within the skill of the art and is merely routine in light of the disclosures herein.

In another preferred embodiment of the method, the E1a gene product is expressed under the control of an inducible promoter and the E1b and E2a genes, as well as any other adenoviral genes (e.g., E4ORF6 and/or VAI RNA) that are present, are expressed under the control of their native promoter. As discussed above, the E1a gene product activates the native promoters of E1b, E2a and any other adenoviral genes. Any inducible promoter can be used so long as expresses low basal levels of E1a when the cell is uninduced and high levels of E1a when the cell is contacted with an inducing agent. A number of inducible promoters are known in the art and have been discussed throughout the specification. Specific inducible promoters include, without limitation, the zinc-inducible sheep metallothionine (MT) promoter; the dexamethasone (Dex)-inducible mouse mammary tumor virus (MMTV) promoter; the ecdysone insect promoter; the tetracycline-repressible system; the tetracycline-inducible system; the RU486-inducible system; and the rapamycin-inducible system.

The following examples illustrate several preferred methods of the invention. These examples are illustrative only and are not intended to limit the scope of the invention.

EXAMPLE 1

AD HELPER GENES AND rAAV PRODUCTION IN B-50 CELLS

A. Plasmids

Plasmid constructions described below involved conventional genetic engineering methods, such as those described in Sambrook et al, cited above.

(1) prAAVCMVLacZ (also prAAVLacZ)

Plasmid prAAVCMVLacZ [see International Patent Application No. WO95/13598 for SEQ ID NO: 1; and Fisher K. J. et al, *J. Virol.*, 70: 520–532 (1996), both incorporated by reference herein] is a rAAV cassette in which AAV rep and cap genes are replaced with a minigene expressing β-galactosidase from a CMV promoter. The linear arrangement of prAAVCMVLacZ includes:

(a) the 5' AAV ITR (bp 1–173) obtained by PCR using pAV2 [C. A. Laughlin et al, *Gene*, 23: 65–73 (1983)] as template [nucleotide numbers 365–538 of SEQ ID NO:1];

(b) a CMV immediate early enhancer/promoter [Boshart et al, *Cell*, 41: 521–530 (1985); nucleotide numbers 563–1157 of SEQ ID NO:1], (c) as optional spacer sequences an SV40 intron (nucleotide numbers 1178–1179 of SEQ ID NO:1), (d) the transgene, *E. coli* beta-galactosidase cDNA (nucleotide numbers 1356–4827 of SEQ ID NO:1), (e) an optional SV40 polyadenylation signal (a 237 BamHI-BclI restriction fragment containing the cleavage/poly-A signals from both the early and late transcription units; nucleotide numbers 4839–5037 of SEQ ID NO:1) and (f) 3' AAV ITR, obtained from pAV2 as a SnaBI-BglII fragment (nucleotide numbers 5053–5221 of SEQ ID NO:1). The remainder of the plasmid is simply plasmid backbone from a pBR322-derivative.

(2) pPGKE1 pPGKE1 is a pUC18-based plasmid into which is inserted a mouse heterologous PGK promoter sequence which regulates the expression of the E1 gene region (m.u. 1.42 to 10.5) from Ad5. This plasmid which was made in the inventors' laboratory also contains a neomycin resistance gene as a selectable marker.

(3) pMMTVE2a pMMTVE2a is a retroviral plasmid in which the dexamethasone-inducible murine mammary tumor virus (MMTV) promoter was placed in regulatory control of the Ad5 E2a gene. The plasmid was constructed as follows. A ClaI/KpnI fragment containing an 1128 bp MMTV promoter sequence and a 2372 bp E2a DBP gene was isolated from pMSGDBP-EN [D. E. Brough et al, *Virol.*, 190: 624–634 (1992)]. This fragment was cloned into a retroviral plasmid pLJ, a pBR322 based plasmid backbone containing the Maloney retrovirus LTRs and a neomycin resistance gene [provided by the inventors' laboratory] at the SalI site after a fill-in reaction.

(4) pCMVORF6 pCMVORF6 is a plasmid containing a CMV immediate early enhancer/promoter sequence which regulates the expression of the E4 ORF6 gene region from Ad5. It was prepared by digesting pCMVβ [Clontech] with NotI, removing the βgal gene, and inserting the ORF6 fragment, prepared by PCR [see, e.g., F. J. Fisher et al, *J. Virol.*, 520–532 (1996)], with fill-in.

(5) pAdVAI pAdVAI is a commercially available plasmid [Promega] which contains the Ad5 VAI gene under the control of its native promoter.

B. Experimental Protocol

Briefly described, B-50 is a cell which stably expresses AAV type 2 rep and cap genes under the control of the homologous p5 promoter. This cell line is characterized by integration of multiple copies (at least 5 copies) of P5-rep-cap gene cassettes in a concatamer form into the host chromosome. This B-50 cell line was deposited with the American Type Culture Collection, 10801 University Boulevard, Manassas, Va. 20110-2209 on Sep. 18, 1997 under Accession No. CRL-12401 pursuant to the requirements of The Budapest Treaty on the International Recognition of the Deposit of Microorganisms for the Purposes of Patent Procedure.

B-50 cells were split and seeded in 60 mm plates at a density of $2 \times 10^5$ cells per plate. Twenty-four hours later, the cells were transfected with a mixture of prAAVCMVLacZ plasmid DNA, and different combinations of the following plasmid DNA constructs: pPGKE1, pMMTVE2a, pCMVORF6 and pVAI (see X-axis in FIG. 1 for details), using DOTAP as transfection reagent (Boehringer Mannheim). The inducing agent, dexamethasone was added at the time of transfection into the medium at a final concentration of 10 $\mu$M.

Ninety-six hours post-transfection, the cells together with transfection medium were harvested by scrapers and subjected to three rounds of freezing-thawing in ethanol-dry ice and 37° C. water bath. The cells were centrifuged at 3000 rpm in a table top centrifuge for 15 minutes at 4° C. One tenth of each lysate was used to infect 84–31 cells, an E1/E4-double complementing cell line which is transducible by rAAV, for 24 hours. The 84–31 cells were then histochemically stained with X-Gal. The numbers of blue cells in each infection were scored and presented on the Y-axis of FIG. 1 as Infectious Units (IU, 1 IU was defined as one blue cell counted) of rAAVLacZ produced in each transfection.

C. AAV Production rAAV was produced at a level of >1000 IU when the cis plasmid carrying the transgene, prAAVLacZ, was transfected in the presence of the AdE1 supplied by pPGKE1, E2a supplied by pMMTVE2a, and the rep/cap supplied by the cell line.

In contrast, all other combinations of adenovirus genes in these cultures either produced no rAAV, or produced less than 300 IU. For example, Column 1 of FIG. 1 describes rAAV produced at a level of <100 IU when the cis plasmid prAAVLacZ carrying the transgene LacZ, was cultured in the presence of the AdE1 supplied by pPGKE1 and the rep/cap proteins were present in the cell in the absence of AdE2a. Column 2 reveals an rAAV production level of <250 IU when the cis plasmid, prAAVLacZ, carrying the same transgene was transfected in the presence of the AdE2a supplied by pMMTVE2a and the rep/cap supplied by the cell but without AdE1. Column 6 reveals an rAAV production level of ~200 IU when the cis plasmid, prAAVLacZ, carrying the same transgene was cultured in the presence of AdE1, AdE2a, Ad E4 ORF6 and the rep/cap supplied by the cell line. Column 7 demonstrates rAAV production of <200 was achieved when the cis plasmid carrying the transgene, prAAVLacZ was cultured in the presence of the AdE1, AdE2a, Ad E4 ORF6 and AdVAI genes in the same cell line. Column 10 reveals rAAV production of about 275 IU when the transgene, AdE2a and AdVAI genes were present in the absence of AdE1. Column 11 reveals an rAAV production of <100 when the transgene, Ad E4ORF6 and AdVAI were present.

No rAAV production was achieved when the cis plasmid carrying the transgene, prAAVLacZ was cultured in the presence of:

(a) the Ad E4 ORF6 gene and in the absence of AdE1 and AdE2a in the same cell line (Col 3);
(b) the Ad VAI gene and in the absence of AdE1 and AdE2a in the same cell line (Col 4);
(c) the Ad E2a, and Ad E4ORF6 genes in the cell line in the absence of E1 (Col. 8);
(d) the Ad E2a, Ad E4ORF6 and AdVAI genes in the cell line in the absence of E1 (Col. 9);
(e) the Ad E1 and AdVAI genes in the cell line in the absence of the E2a gene (Col. 12); and
(f) the Ad E1 and AdE4 ORF6 genes in the cell line in the absence of the E2a gene (Col. 13).

Clearly the provision of the transgene in the cis acting plasmid, AAV rep and cap sequences by the cell line and the AdE1 and AdE2a genes in a transacting plasmid resulted in a dramatic production level of rAAV.

EXAMPLE 2

MOLAR RATIO OF E1 TO E2A GENE-CONTAINING PLASMIDS AND rAAV PRODUCTION IN B-50 CELLS

To optimize rAAV productivity by helper-free B-50/transfection system, B-50 cells were seeded at a density of $2 \times 10^5$ cells per 60 mm plate for 24 hours and then transfected with prAAVLacZ, and a mixture of pPGKE1 and pMMTVE2a plasmid DNAs at different molar ratios: 2.6:1, 0.9:1, 5.2:1, and 1.3:1. Ninety-six hours post-transfection, the cell lysates were prepared and the rAAVLacZ in each lysate was titered as described in Example 1.

Figure 2:
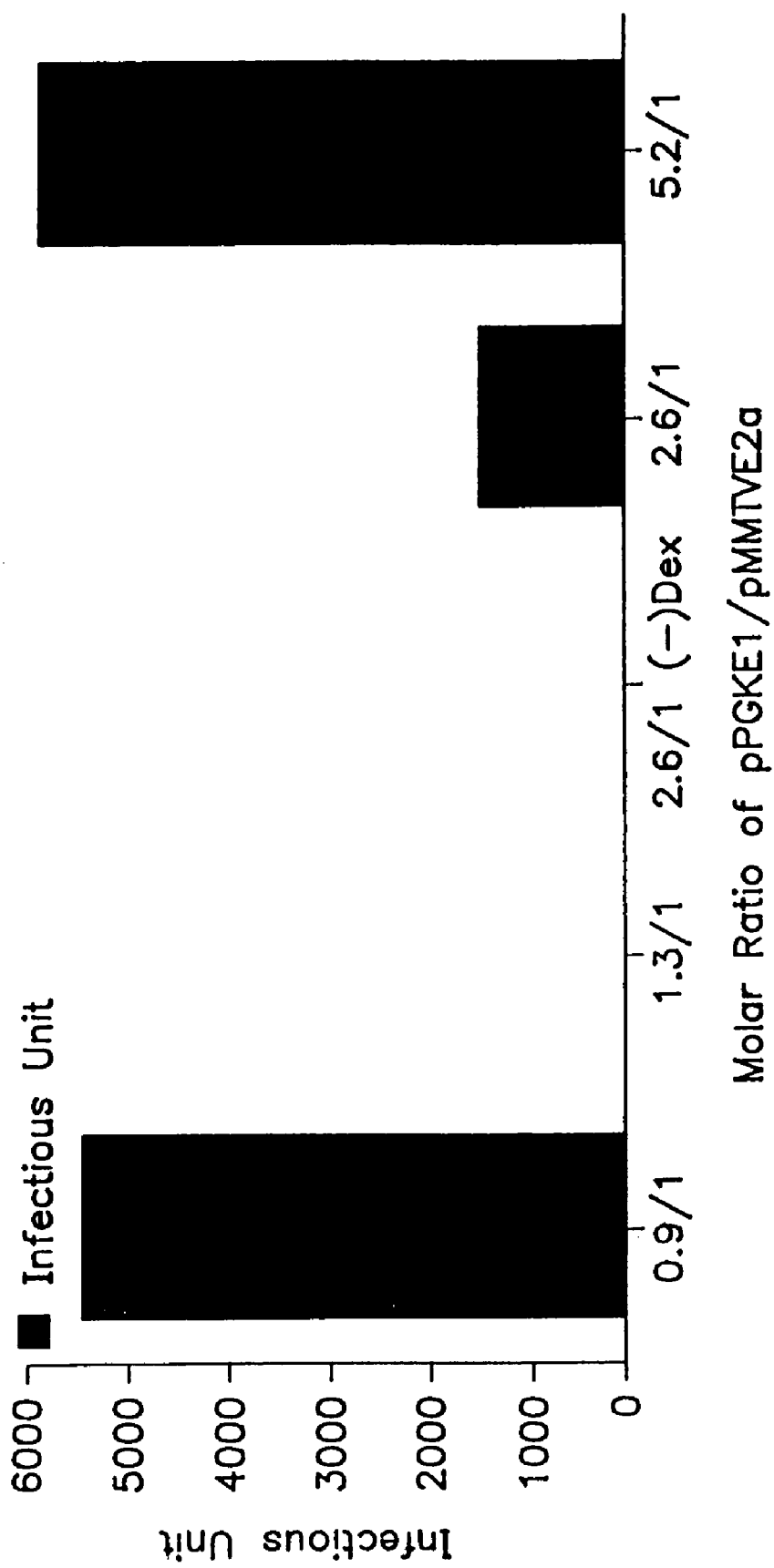
FIG. 2 is a bar graph which plots IU of rAAV produced in the presence of different molar ratios of the plasmids pPGKE1 and pMMTVE2a in B-50 cells. The molar ratios are reported under the X axis. See, e.g., Example 2.

The results which are shown in the bar graph of FIG. 2 illustrate that there are preferred molar ratios of the E1 containing plasmids to the E2a containing plasmids which permit enhanced production of the rAAV according to the method of this invention. Under these particular experimental conditions, the maximum rAAV production was obtained when the ratio was either 5.2:1 or 0.9:1 in the presence of dexamethasone, the inducing agent for the MMTV promoter which controls the expression of E2a. As shown in FIG. 2, in the absence of the inducing agent, i.e., no E2a production, no rAAV was produced. Curiously, no rAAV was produced when the ratio was 1.3:1, although the ratio of 2.6:1 produced a good amount of rAAV. This result is assumed to be due to differences in the efficiencies of the transfections.

EXAMPLE 3

HELPER-FREE rAAV PRODUCTION IN A549 CELLS

To verify the discovery that only Ad E1 and E2 genes are necessary to provide helper functions for rAAV production, the method of the present invention was attempted in other mammalian cell lines, such as HEK293 cells which have integrated therein an E1 gene under a constitutive promoter, and A549 (human lung carcinoma) cells, which contain no adenovirus genes.

P5-Rep/Cap is a plasmid used in this experiment which carries the AAV rep and cap sequences under the control of the native AAV promoter P5. This plasmid was constructed as follows: the MT promoter and ORF6 sequences were removed from pMTE4ORF6 plasmid [G. P. Gao et al, *J. Virol.*, 70: 8934–8943 (1996)] by EcoRI/BamHI digestion and replaced with a 4.3 kb P5-Rep/Cap fragment which was isolated from pSub201 plasmid [Samulski, R. J. et al, *J. Virol.*, 63: 3822–3828 (1989)] by XbaI digestion. Plasmid construction involved conventional genetic engineering methods, such as those described in Sambrook et al, cited above.

A culture of each type of cells, HEK293 and A549, was co-transfected with prAAVCMVLacZ, and a mixture of pP5-Rep/Cap (also referred to as pTrans), pPGKE1 and pMMTVE2a at different molar ratios. The molar ratios of Rep/Cap to E1-containing plasmid to E2a containing plasmid were as follows: 3.2:2.6:1; 3.2:5.2:2; 3.2:7.8:1; 1.6:2.6:4; 1.6:10.4:1; 1.6:0:5 (i.e., no E1); 1.6:13:0 (i.e., no E2a); and 3.2:0:4 (i.e., no E1). pAdWt (a plasmid DNA containing an intact Ad5 genome) served as a positive control. As described above, the inducing agent, dexamethasone, was added to the medium at the time of transfection at a final concentration of 10 $\mu$M. Ninety-six hours post-transfection, the cell lysates were prepared.

The rAAVLacZ produced in each transfection was titered as described in Example 1. In this experiment, co-transfection of HEK 293 cells with pP5-Rep/Cap, prAAVCMV-LacZ, pPGKE1 and pMMTVE2a did not generate any rAAVLacZ at any of the molar ratios. This is believed to be due to over-expression of the E1 gene product prior to the introduction of the inducing agent, dexamethasone, for the E2a plasmid.

Figure 3:
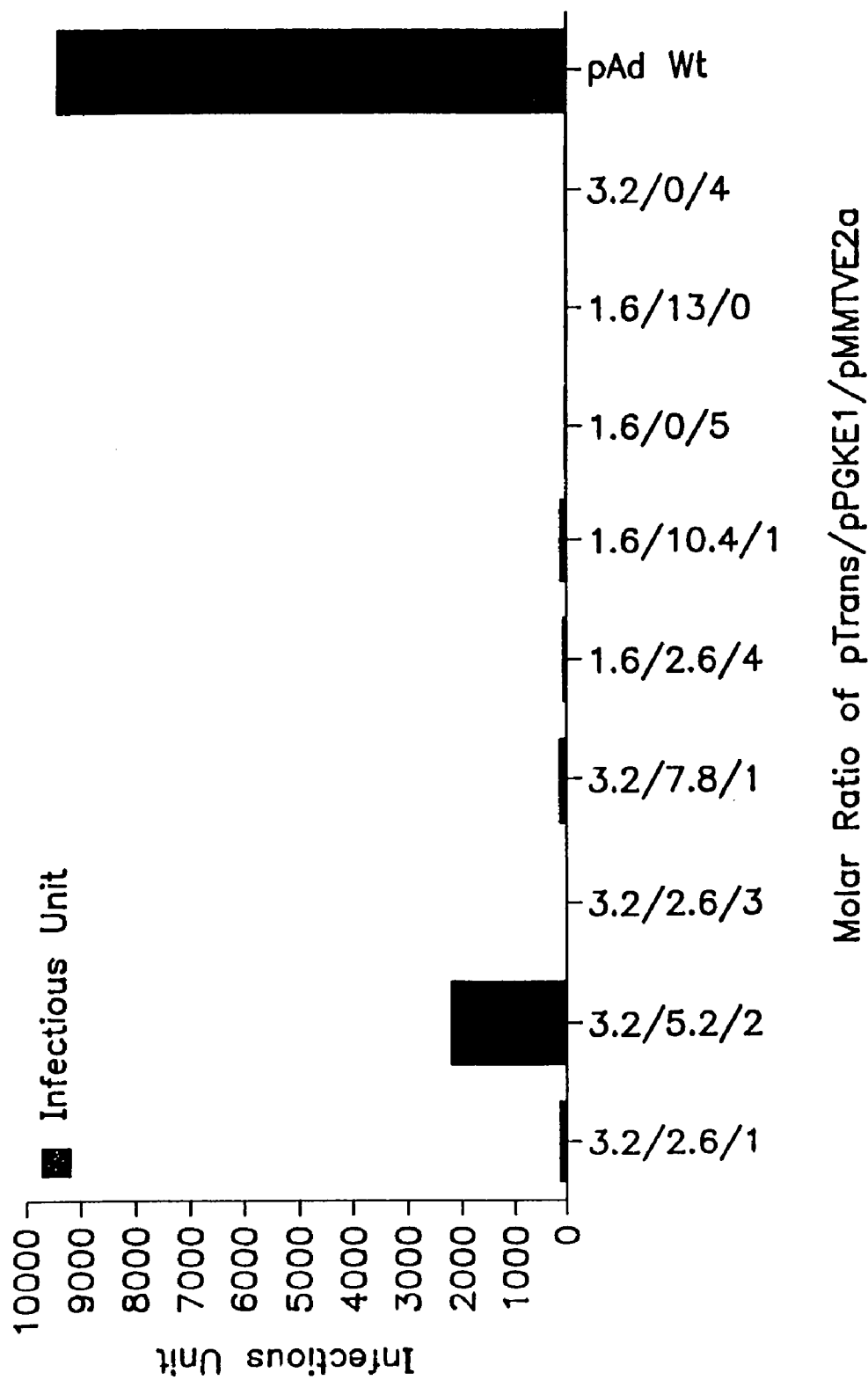
FIG. 3 is a bar graph which plots IU of rAAV produced in the presence of AAV rep/cap, Ad E1 gene product and Ad E2a gene product in A549 human lung carcinoma cells. The X axis shows the molar ratios of the plasmids pP5-Rep/Cap: pPGKE1: pMMTVE2a used in this experiment. pAdWt (a plasmid DNA containing an intact Ad5 genome) served as a positive control.

As depicted in FIG. 3, this method using the ratio of 3.2/5.2/2 produced about 2000 infectious units of rAAV in A549 cells. Note that with a plasmid containing the entire complement of Ad helper genes, pAdWt, over 9000 infectious units of rAAV were produced.

These results demonstrate that the adenovirus E1 and E2a genes provide sufficient helper function to permit rAAV production in A549 cells transfected with AAV rep/cap and the cis plasmid containing the transgene.

EXAMPLE 4

USE OF INDUCIBLE E1 AND HYBRID AD/AAV VECTOR TO PRODUCE rAAV IN B-50 CELLS

B-50 cells are stably transfected with a plasmid containing the E1 gene operably linked to an inducible promoter. If the inducible promoter is rapamycin-inducible [Magari et al. *J. Clin. Invest.*, 100: 2865–2872 (1997)], ecdysone-inducible [No et al, *Proc. Natl. Acad. Sci. USA*, 93: 3346–3351 (1996)], RU486-inducible [Wang et al., *Nat. Biotech.* 15: 239–243 (1997) and Wang et al., *Gene Ther.*, 4: 432–441 (1997)], tet-inducible [Gossen et al., *Science*, 268: 1766–1769 (1995)] or tet-repressible [Gossen et al., *Proc. Natl. Acad. Sci. USA*, 89: 5547–5551 (1992); Rossi et al., *Nat. Genet.*, 20: 389–393 (1998)], a vector encoding the appropriate activator and/or repressor factor (depending upon the system) is also stably transfected into the B-50 cells as described in the references. The B-50 cells contain the neomycin resistance gene and are resistant to G-418 (Geneticin). Thus, the plasmids encoding the inducible E1 and the activator and/or repressor factors must contain a different selectable marker than neomycin. Exemplary selectable markers are hygromycin or puromycin resistance. Stable transfectant colonies are selected in the presence of culture media containing the appropriate antibiotic (i.e., either hygromycin or puromycin) and are expanded individually. Individual clones are evaluated on the criteria that E1 is substantially absent when the inducer is not present and that E1 is present at high levels when the inducer is present. Clones are also evaluated for the ability of the induced E1 to activate rep and cap gene expression in the B-50 cells.

B-50 cells are seeded at a density of $2 \times 10^5$ cells per 60 mm plate for 24 hours. Twenty-four hours later, the seeding media (DMEM/10% FBS supplemented with antibiotics) is replaced with DMEM/2% FBS and the inducing agent for the inducible E1a promoter. The cells are infected with Ad.AV.CMVLacZ hybrid clones at an appropriate MOI. The Ad.AV.CMVLacZ hybrid is described in U.S. Pat. No. 5,856,152. The Ad/AV.CMVLacZ hybrid is essentially is an adenovirus which contains a recombinant AAV genome (AV.CMVLacZ) replacing the E1a and E1b Ad5 sequences, wherein the recombinant AAV genome has a linear arrangement of:

(a) the 5' AAV-2 ITR (bp 1–173);
(b) a CMV immediate early enhancer/promoter;
(c) an SV40 intron;
(d) E. coli beta-galactosidase cDNA;
(e) an SV40 polyadenylation signal (a 237 Bam HI-BclI restriction fragment containing the cleavage/poly-A signals from both the early and late transcription units; and
(f) 3'AAV ITR, obtained from pAV2 as a SnaBI-BglII fragment.

In alternative embodiments, the CMV promoter (b) may be replaced by a different inducible, constitutive, tissue-specific or native promoter; the SV40 intron (c) and SV40 polyadenylation signal (e) may be replaced by other introns and polyadenylation signals or may be deleted; and the beta-galactosidase cDNA (d) may be replaced by any other gene, including another marker gene or a therapeutic gene.

Twenty-four hours to ninety-six hours after infection, the cell lysates are prepared and the rAAVLacZ in each lysate is titered as described in Example 1.

In an alternative embodiment, the inducing agent is added 24 hours after infection of the cells with the Ad/AAV hybrid.

In other embodiments, the Ad/AAV hybrid contains, in addition to the rAAV sequences, only the E2a gene, E4ORF6 and/or VAI RNA adenoviral genes. In this embodiment, even if the E2a gene is included in the Ad/AAV hybrid, the E2a gene is also included on the vector containing the inducible E1 gene. The vector containing the inducible E1 gene may also contain one or more of E4ORF6 or VAI RNA.

EXAMPLE 5

USE OF INDUCIBLE E1 AND rAAV VECTOR TO AMPLIFY rAAV IN B-50 CELLS

B-50 cells are stably transfected with a vector containing the E1 gene operably linked to an inducible promoter and evaluated for expression as discussed in Example 4. The vector containing the inducible E1 preferably contains E2a, and may include E4ORF6 and/or VAI RNA. In a preferred embodiment, the E2a and the optional E4ORF6 and VAI RNA are under the control of their native promoters.

B-50 cells are seeded at a density of $2 \times 10^5$ cells per 60 mm plate for 24 hours. Twenty-four hours later, the seeding media (DMEM/10% FBS supplemented with antibiotics) is replaced with DMEM/2% FBS and the inducing agent for the inducible E1a promoter. The cells are infected with rAAVLacZ that is free of rcAAV at an appropriate MOI. The rAAVLacZ may be produced by any method known in the art, such as that described in Example 4.

Twenty-four hours to ninety-six hours after infection, the cell lysates are prepared and the rAAVLacZ in each lysate is titered as described in Example 1.

EXAMPLE 6

USE OF B-50 CELLS TO DEVELOP HELPER INDEPENDENT PRODUCER CELL LINES FOR rAAV

B-50 cells are stably transfected with a vector containing the E1 gene operably linked to an inducible promoter and evaluated for expression as discussed in Example 4. The vector also contains, at the least, the E2a gene and rAAV. The vector containing E1, E2a and rAAV may also contain E4ORF6 and VAI RNA. The promoter for the E2a and the optional E4ORF6 and VAI RNA genes are preferably their native promoters.

B-50 cells are seeded at a density of $2 \times 10^5$ cells per 60 mm plate for 24 hours. Twenty-four hours later, the seeding media (DMEM/10% FBS supplemented with antibiotics) is replaced with DMEM/2% FBS and the inducing agent for the inducible E1a promoter. The inducer turns on E1 expression which in turn triggers expression of the other adenoviral genes, rep and cap expression and subsequent rAAV production.

Twenty-four hours to ninety-six hours after induction, the cell lysates are prepared and the lysate is titered for rAAV production by any process known in the art. If the rAAV is rAAVLacZ, the lysate can titered as described in Example 1.

EXAMPLE 7

PRODUCTION OF HELPER INDEPENDENT CELL LINE FOR PRODUCTION OF rAAV

Cells from a cell line (e.g., A549, HeLa, 3T3, 10T1/2, HT1080 or HepG2) are stably transfected with a vector containing the E1 gene operably linked to an inducible promoter and evaluated for expression as discussed in Example 4. The vector also contains, at the least, the E2a gene, rAAV and the rep and cap gene. The vector may also contain E4ORF6 and VAI RNA. The promoter for the E2a and the optional E4ORF6 and VAI RNA genes are preferably their native promoter. The promoter for rep and cap is preferably the P5 promoter. The selectable marker for transfection may be neomycin or hygromycin resistance.

The stably transfected cells are seeded at a density of $2 \times 10^5$ cells per 60 mm plate for 24 hours. Twenty-four hours later, the seeding media (DMEM/10% FBS supplemented with antibiotics) is replaced with DMEM/2% FBS and the inducing agent for the inducible E1a promoter. The inducer turns on E1 expression which in turn triggers expression of the other adenoviral genes, rep and cap expression and subsequent rAAV production.

Twenty-four hours to ninety-six hours after induction, the cell lysates are prepared and the lysate is titered for rAAV production by any process known in the art. If the rAAV is rAAVLacZ, the lysate can titered as described in Example 1.

EXAMPLE 8

USE OF THE B-50 CELL LINE AND AD/AAV HYBRID VECTOR FOR PRODUCTION OF A HELPER INDEPENDENT CELL LINE

A recombinant Ad/AAV hybrid vector is constructed using the methods described in U.S. Pat. No. 5,856,152 except that the E3 gene is deleted and the E1 gene operably linked to and under the control of the RSV or PGK promoter is cloned into the E3 region of the adenovirus genome. The Ad/AAV hybrid vector is packaged as described in U.S. Pat. No. 5,856,152.

B-50 cells are seeded at a density of $2 \times 10^5$ cells per 60 mm plate for 24 hours. Twenty-four hours later, the seeding media (DMEM/10% FBS supplemented with antibiotics) is replaced with DMEM/2% FBS. The cells are infected with recombinant Ad/AAV clone containing E1 and the rAAV minigene at an appropriate MOI. This one step infection of B-50 cells provides all the helper genes required for rAAV production. Thus, there will be no need for other helper viruses such as sub100r.

Twenty-four hours to ninety-six hours after infection, the cell lysates are prepared and the lysate is titered for rAAV production by any process known in the art. If the rAAV is rAAVLacZ, the lysate can titered as described in Example 1.

EXAMPLE 9

USE OF THE B-50 CELL LINE AND AD/AAV HYBRID VECTOR FOR PRODUCTION OF A HELPER INDEPENDENT CELL LINE

A recombinant Ad/AAV hybrid vector is constructed using the methods described in U.S. Pat. No. 5,856,152 with the following changes:

(a) the E3 gene of the adenovirus is deleted and is replaced with a nucleic acid sequence comprising the AAV ITRs, the transgene and the transgene's associated regulatory sequences;

(b) the E1 gene of the adenovirus is not deleted; and (c) an inducible promoter, including, without limitation, one described above (i.e., the metallothionine (MT) promoter the dexamethasone (Dex)-inducible MMTV promoter, the T7 polymerase promoter system, the ecdysone insect promoter, the tetracycline-repressible system, the tetracycline-inducible system, the RU486-inducible system and the rapamycin-inducible system) is operably linked to the native E1a gene and the native E1b promoter remains intact to regulate the expression of the E1b gene. In an alternative embodiment, the native E1a and E1b promoters are used.

The Ad/AAV hybrid vector is packaged as described in U.S. Pat. No. 5,856,152.

B-50 cells are seeded at a density of $2 \times 10^5$ cells per 60 mm plate for 24 hours. Twenty-four hours later, the seeding media (DMEM/10% FBS supplemented with antibiotics) is replaced with DMEM/2% FBS and the inducing agent for the inducible E1a promoter. The inducer turns on E1a expression which in turn triggers expression of E1b, the other adenoviral genes, rep and cap expression and subsequent rAAV production. If the native E1a promoter is used, the inducing agent is not be necessary. The cells are infected with recombinant Ad/AAV clone containing the E1 adenovirus gene and the rAAV minigene at an appropriate MOI. This one step infection of B-50 cells provides all the helper genes required for rAAV production. Thus, there will be no need for other helper viruses such as sub100r.

Twenty-four hours to ninety-six hours after induction and infection, the cell lysates are prepared and the lysate is titered for rAAV production by any process known in the art. If the rAAV is rAAVLacZ, the lysate can titered as described in Example 1.

All documents cited above are herein incorporated by reference. Numerous modifications and variations of the present invention are included in the above-identified specification and are expected to be obvious to one of skill in the art. Such modifications and alterations to the processes of the present invention are believed to be encompassed in the scope of the claims appended hereto.

What is claimed is:

1. A mammalian host cell useful for producing rAAV in the absence of a helper adenovirus comprising;
   (a) a transgene under the control of regulatory sequences directing expression thereof and flanked by AAV inverted terminal repeats;
   (b) an AAV rep sequence and an AAV cap sequence under the control of regulatory sequences directing expression thereof; and
   (c) adenovirus sequences consisting of the minimum adenovirus DNA required to express an E1a gene product, an E1b gene product, and an E2a gene product;
   wherein the only adenovirus gene products expressed in the host cell are adenovirus E1a, E1b and E2a.

2. The host cell according to claim 1 wherein said transgene regulatory sequences comprise a promoter selected from the group consisting of a native promoter of the transgene, an inducible promoter, a tissue-specific promoter and a constitutive promoter.

3. The host cell according to claim 1, wherein said DNA which expresses said E1a gene product is operably linked to a first promoter directing the expression of said E1a gene product;
   said DNA which expresses said E1b gene product is operably linked to a second promoter directing the expression of said E1b gene product; and
   said DNA which expresses said E2a gene product is operably linked to a third promoter directing the expression of said E2a gene product.

4. The host cell according to claim 3, wherein said first promoter is selected from the group consisting of a native promoter of E1a, an inducible promoter and a constitutive promoter; wherein said second promoter is selected from the group consisting of a native promoter of E1b, an inducible promoter and a constitutive promoter; and wherein said third promoter is selected from the group consisting of a native promoter of E2a, an inducible promoter and a constitutive promoter.

5. The host cell according to claim 3, wherein said first promoter and said third promoter are not identical.

6. The host cell according to claim 3, wherein said first promoter and said third promoter are identical.

7. The host cell according to claim 3 wherein said first promoter and said third promoter are inducible promoters.

8. The host cell according to claim 3 wherein said first promoter or said third promoter is an inducible promoter.

9. The host cell according to claim 1, wherein said transgene of (a) is stably integrated into the chromosome of said host cell, present in said host cell as an episome, or transiently expressed in said host cell;

said AAV rep and cap genes of (b) are stably integrated into the chromosome of said host cell, present in said host cell as an episome, or transiently expressed in said host cell; and said DNA of (c) is stably integrated into the chromosome of said host cell, present in said host cell as an episome, or transiently expressed in said host cell.

10. The host cell according to claim 1, wherein said transgene is supplied to said host cell by a rAAV.

11. The host cell according to claim 1, wherein said transgene and said DNA required to express said E1a gene product and said E1b gene product are supplied to said host cell on the same vector.

12. A method for producing recombinant adeno-associated virus (rAAV) in the absence of contaminating helper virus or wild-type virus, comprising the step of culturing the host cell of claim 1, wherein the only adenovirus gene products expressed in the host cell are adenovirus E1a, E1b and E2a.

13. The method according to claim 12, further comprising the step of purifying the rAAV from said host cell or host cell culture.

14. The method according to claim 13, wherein said minimum adenovirus DNA required to express an E1a gene product is operably linked to a first promoter selected from the group consisting of an inducible promoter, a constitutive promoter and a native promoter for E1a;

said minimum adenovirus DNA required to express an E1b gene product is operably linked to a second promoter selected from the group consisting of an inducible promoter, a constitutive promoter and a native promoter for E1b; and said minimum adenovirus DNA required to express an E2a gene product is operably linked to a third promoter selected from the group consisting of an inducible promoter, a constitutive promoter and a native promoter for E2a.

15. The method according to claim 14, wherein at least one promoter of said first promoter, second promoter or third promoter is an inducible promoter, further comprising the step of adding to said host cell culture a first inducing agent to induce said inducible promoter.

16. The method according to claim 14, wherein said first and third promoters are different inducible promoters directing the expression of each respective gene product.

17. The method according to claim 16 further comprising the steps of adding to said host cell culture a first inducing agent for inducing said first inducible promoter and a second inducing agent for inducing said second inducible promoter, whereby the ratio of expressed gene products may be varied for optimizing the production of rAAV in said host cells.

18. A preparation of recombinant adeno-associated virus (rAAV) in the presence of host cells, absent contaminating helper virus or wild-type virus, prepared by the method of culturing said host cells, said host cells comprising:

(i) a transgene under the control of regulatory sequences directing expression thereof and flanked by AAV inverted terminal repeats;

(ii) an AAV rep sequence under the control of regulatory sequences directing expression thereof;

(iii) an AAV cap sequence under the control of regulatory sequences directing expression thereof; and (iv) adenovirus sequences consisting of the minimum adenoviral DNA required to express an E1a gene product, an E1b gene product, and an E2a gene product;

wherein the only adenovirus gene products expressed in the host cell are adenovirus E1a, E1b and E2a.

19. The preparation of claim 18, wherein the adenovirus gene products are transiently produced in the host cell.

20. The preparation of claim 18, wherein the adenovirus gene products are delivered via a plasmid.

* * * * *

UNITED STATES PATENT AND TRADEMARK OFFICE
CERTIFICATE OF CORRECTION

PATENT NO. : 6,953,690 B1  
APPLICATION NO. : 09/665852  
DATED : October 11, 2005  
INVENTOR(S) : Guangping Gao and James M. Wilson It is certified that error appears in the above-identified patent and that said Letters Patent is hereby corrected as shown below:

Title Page, Item "(*) Notice", replace "98 days" with -- 71 days --.

Signed and Sealed this

Twelfth Day of February, 2008

JON W. DUDAS  
*Director of the United States Patent and Trademark Office*